(12) United States Patent
Suh et al.

(10) Patent No.: US 10,842,519 B2
(45) Date of Patent: Nov. 24, 2020

(54) VACUUM-ACTUATED SURGICAL GRASPERS

(71) Applicant: The Regents of the University of California, Oakland, CA (US)

(72) Inventors: Insoo Suh, Oakland, CA (US); Orlo H. Clark, Oakland, CA (US); Sachin Rangarajan, Oakland, CA (US); Isabelle Chumfong, Oakland, CA (US); Romain Christophe Roux, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/772,857

(22) PCT Filed: Nov. 2, 2016

(86) PCT No.: PCT/US2016/060117
§ 371 (c)(1),
(2) Date: May 2, 2018

(87) PCT Pub. No.: WO2017/079300
PCT Pub. Date: May 11, 2017

(65) Prior Publication Data
US 2018/0317948 A1    Nov. 8, 2018

Related U.S. Application Data

(60) Provisional application No. 62/249,660, filed on Nov. 2, 2015.

(51) Int. Cl.
*A61B 17/30* (2006.01)
*A61B 17/00* (2006.01)
(Continued)

(52) U.S. Cl.
CPC ........ *A61B 17/30* (2013.01); *A61B 17/00234* (2013.01); *A61B 17/0218* (2013.01);
(Continued)

(58) Field of Classification Search
CPC .......... A61B 17/30; A61B 2017/00438; A61B 17/0218
See application file for complete search history.

(56) References Cited

U.S. PATENT DOCUMENTS

| 4,519,385 | A | | 5/1985 | Atkinson et al. |
| 5,203,769 | A | * | 4/1993 | Clement ............ A61B 18/1482 251/309 |

(Continued)

OTHER PUBLICATIONS

International Search Report for PCT/US2016/060117 dated Nov. 2, 2016.

(Continued)

*Primary Examiner* — Ellen C Hammond
*Assistant Examiner* — Tara Rose E Carter
(74) *Attorney, Agent, or Firm* — Thomas Horstemeyer, LLP

(57) ABSTRACT

In one embodiment, a vacuum-actuated surgical grasper includes a suction head adapted to interface with patient tissue, a suction tube connected to and in fluid communication with the suction head, and a handle connected to the suction tube, the handle comprising an internal passage in fluid communication with the suction tube through which fluid from the suction tube can flow and a pivotable actuation lever that controls this flow through the passage.

4 Claims, 11 Drawing Sheets

(51) Int. Cl.
*A61B 17/22* (2006.01)
*A61B 17/02* (2006.01)

(52) U.S. Cl.
CPC ............... *A61B 17/22031* (2013.01); *A61B 2017/00438* (2013.01); *A61B 2017/00561* (2013.01); *A61B 2017/306* (2013.01); *A61B 2217/005* (2013.01)

(56) References Cited

U.S. PATENT DOCUMENTS

| | | |
|---|---|---|
| 5,273,524 A | 12/1993 | Fox et al. |
| 5,336,172 A | 8/1994 | Bales et al. |
| 5,417,709 A | 5/1995 | Slater |
| 5,549,547 A | 8/1996 | Cohen |
| 5,593,135 A | 1/1997 | Lester et al. |
| 6,066,150 A | 5/2000 | Gonon |
| 6,090,041 A | 7/2000 | Clark et al. |
| 7,727,117 B2 | 6/2010 | Feldman et al. |
| 7,811,256 B2 | 10/2010 | Landman et al. |
| 7,967,774 B2 | 6/2011 | Bayat |
| 2010/0256662 A1 | 10/2010 | Racenet et al. |
| 2011/0251459 A1* | 10/2011 | Ferreira ............... A61B 1/015 600/118 |
| 2015/0142032 A1 | 5/2015 | Scheib et al. |

OTHER PUBLICATIONS

Insoo Suh et al., The Lamprey: A novel surgical device for atraumatic retraction and manipulation of soft tissue, University of California San Francisco (UCSF) Sep. 10, 2015, 27 pages.

\* cited by examiner

VACUUM-ACTUATED SURGICAL GRASPERS

CROSS-REFERENCE TO RELATED APPLICATIONS

This application is the 35 U.S.C. § 371 national stage application of PCT Application No. PCT/US2016/060117, filed Nov. 2, 2016, where the PCT claims the benefit of and priority to U.S. Provisional Application Ser. No. 62/249,660, filed Nov. 2, 2015, both of which are hereby incorporated by reference in their entireties.

BACKGROUND

Mechanical surgical graspers have been used for decades in surgical procedures to manipulate (e.g., retract) patient tissues. Such graspers typically take the form of forceps that include a scissors-like handle that is used to open and close opposing jaws that can grip the tissue.

While such mechanical graspers are generally effective, their jaws can damage delicate tissues of a patient. Because of this, a vacuum-actuated surgical grasper described in U.S. Pat. No. 6,090,041 ("the '041 patent"), which is hereby incorporated by reference into the present disclosure, was developed. Instead of using opposed jaws to grip tissue, the vacuum-actuated surgical grasper of the '041 patent uses a suction head to apply gentle suction to the tissue to grip it. This grasper reduces the likelihood of the tissue being damaged when retracted or otherwise manipulated.

Although the vacuum-actuated surgical grasper described in the '041 patent provides advantages over conventional mechanical graspers, the way in which it is used is not the same as mechanical graspers typically used in surgical procedures. Instead of having a scissors-like handle that can be used to modulate the grasping force, the vacuum-actuated grasper of the '041 patent simply comprises an elongated tube that the surgeon grasps, which provides no means for modulating the grasping force.

From the above discussion it can be appreciated that it would be desirable to have a vacuum-actuated surgical grasper that can be operated in a manner similar to that with which a conventional mechanical grasper is operated.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a vacuum-actuated surgical grasper that can be operated in a manner similar to that with which a conventional mechanical grasper is operated. Examples of such vacuum-actuated surgical graspers are described in the disclosure that follows. In some embodiments, the graspers comprise a handle that includes an actuation lever that can be pivoted to actuate the grasper. In an initial, unactuated position of the actuation lever, no suction is provided to the suction head of the grasper. As the actuation lever is pivoted away from the initial position, however, suction is delivered to the suction head that can be used to grip tissue. In some embodiments, the suction strength linearly increases as the actuation lever is moved away from its initial position.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
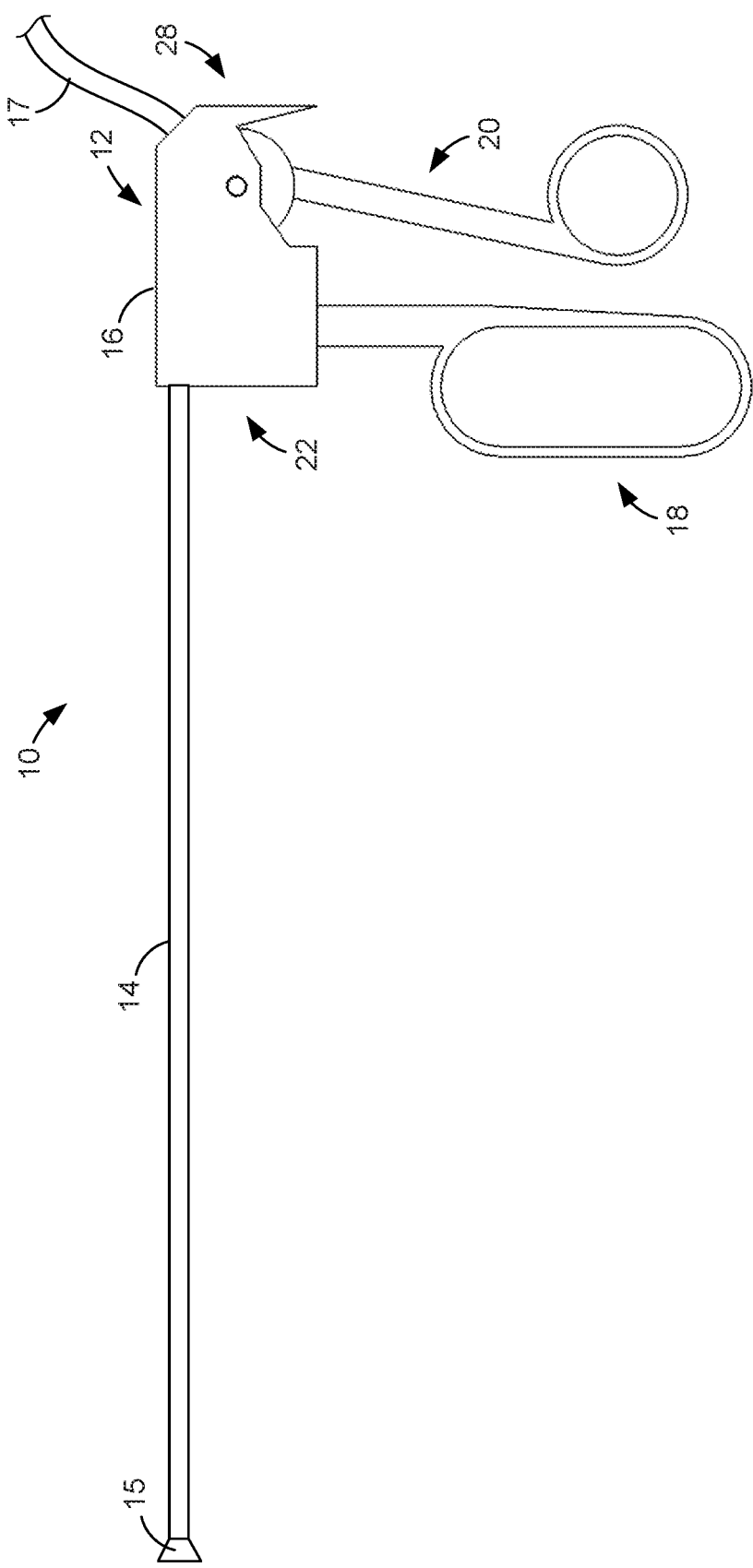
FIG. 1 is a side view of a first embodiment of a vacuum-actuated surgical grasper.

FIG. 1 illustrates a first embodiment of a vacuum-actuated surgical grasper 10 that can be used in a surgical procedure, such as a laparoscopic procedure. As shown in the figure, the grasper 10 generally comprises a handle 12 and an elongated rigid suction tube 14 that extends from the handle having a suction head 15 provided on its distal tip. As is discussed in greater detail below, the grasper 10 is adapted to connect to a vacuum source, for instance via a tube 17, and deliver suction to the suction head. Specific examples of suitable suction heads are described in U.S. Pat. No. 6,090,041, which has been incorporated by reference. The handle 12 is used by the user, such as a surgeon, to hold the grasper 10 during use. In addition, the handle 12 is used to control the amount of suction applied to tissue that is to be grasped by the grasper 10.

Figure 2:
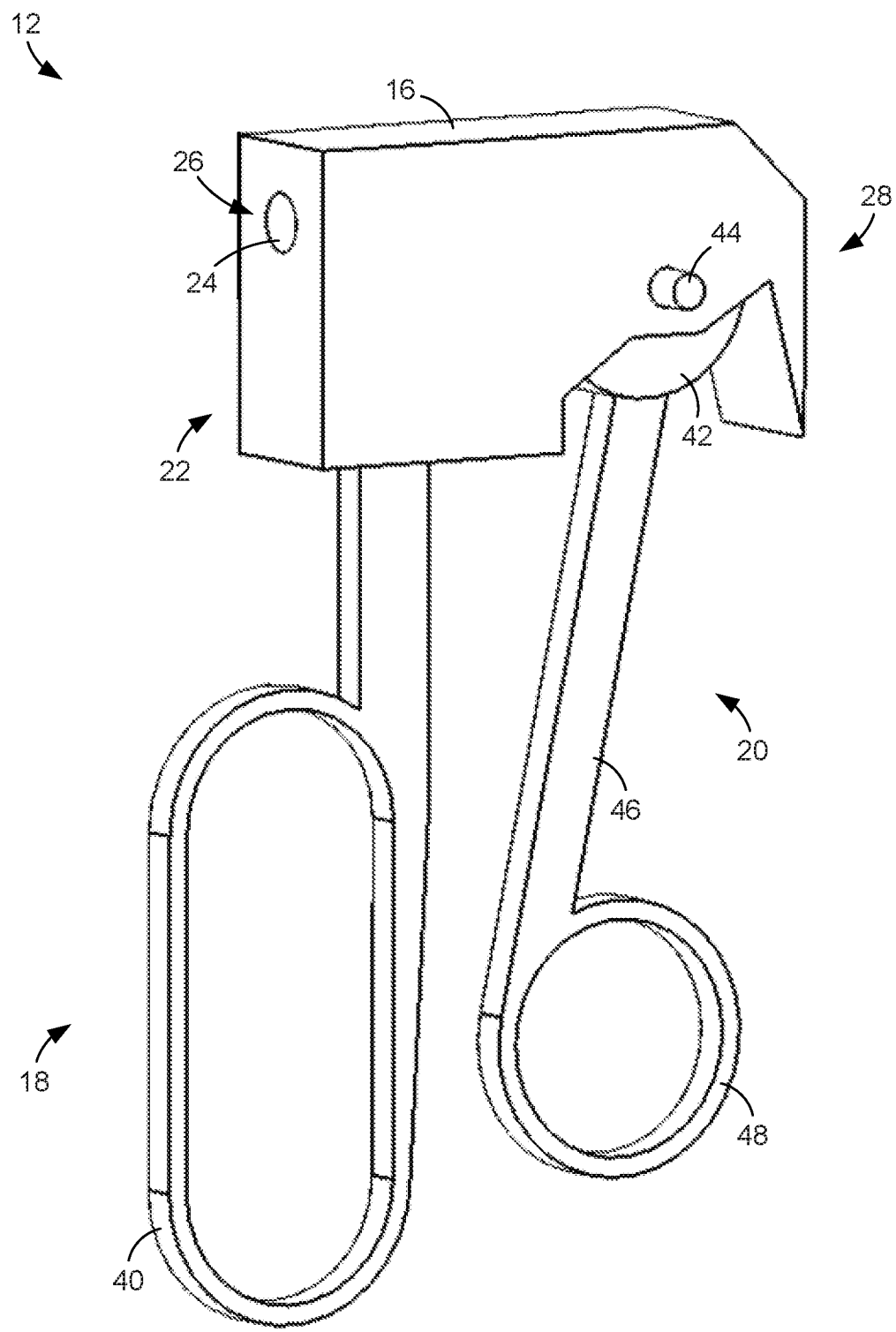
FIG. 2 is a front perspective view of a first embodiment of a handle of the grasper of FIG. 1.
Figure 3:
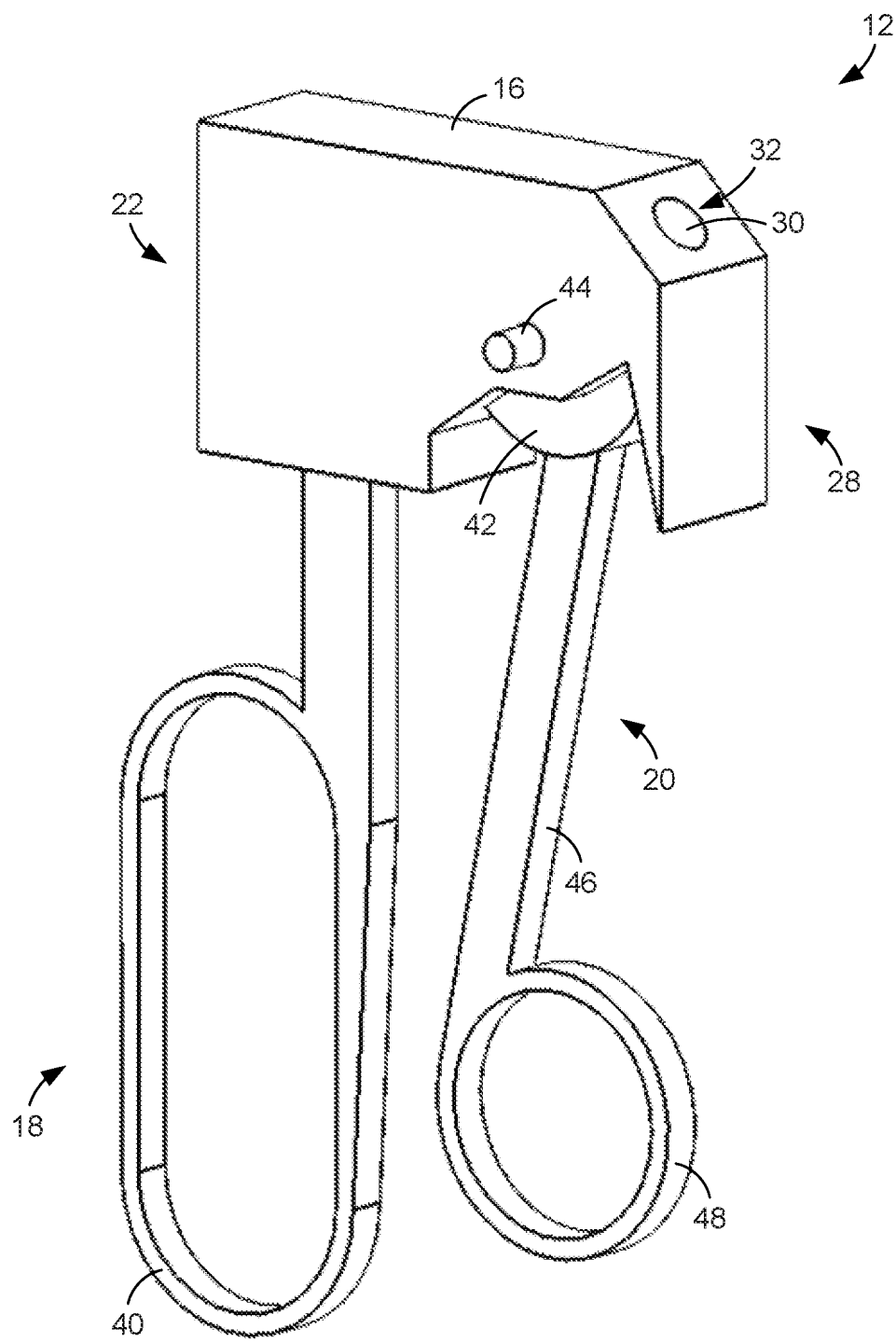
FIG. 3 a rear perspective view of the grasper handle of FIG. 2.

As shown most clearly in the views of FIGS. 2 and 3, which show the handle separate from the suction tube 14, the handle includes a body 16 from which the suction tube, a grip element 18, and an actuation lever 20 extend. When the grasper 10 is fully assembled, the tube 14 is placed in fluid communication with an internal passage of the handle 12 that passes through the body 16 through which fluid, such as a gas (e.g., air), can flow to enable the application of suction to the suction head 15 and, therefore, patient tissue.

FIG. 2 shows the distal end 22 of the handle body 16. As indicated in this figure, a first or distal channel 24 is formed in the body 16 that can be accessed through an inlet port 26 to which the suction tube 14 connects. FIG. 3 shows the proximal end 28 of the handle body 16. As indicated in this figure, a second or proximal channel 30 is formed in the body 16 that can be accessed through an outlet port 32 to which a vacuum source can be connected (e.g., with the tube 17 shown in FIG. 1).

Figure 4:
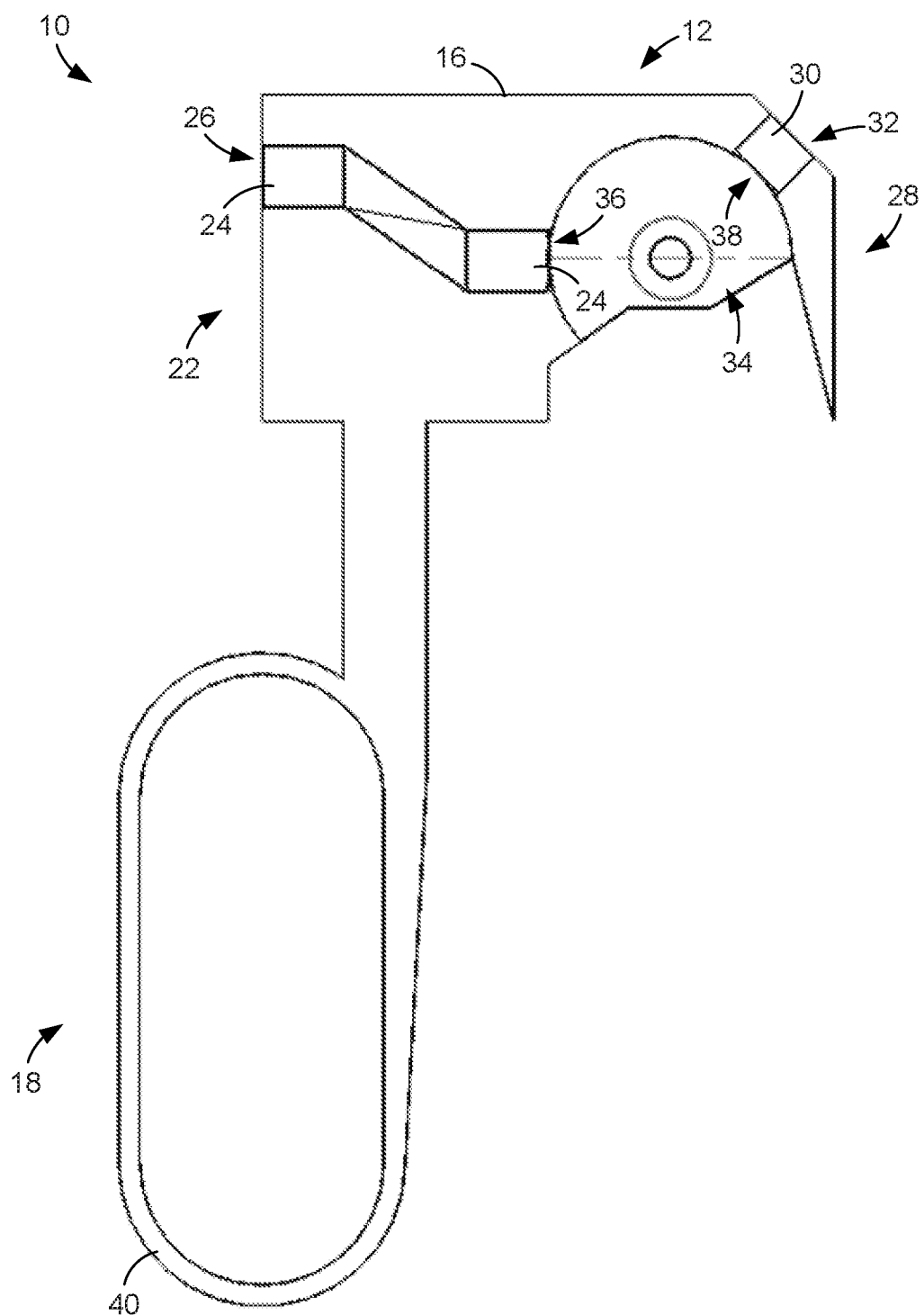
FIG. 4 is a cross-sectional side view of the grasper of FIG. 1 taken along the sagittal plane of the grasper, the grasper shown with an actuation lever of the grasper removed.

FIG. 4 shows the handle body 16 in cross-section with the actuation lever 20 removed and therefore reveals a semicircular cavity 34 that a head of the lever occupies when the grasper 10 is fully assembled. As shown in FIG. 4, the distal channel 24 is in fluid communication with the cavity 34 via an outlet port 36 and the proximal channel 30 is in fluid communication with the cavity via an inlet port 38. From this figure, it can be appreciated that a fluid, such as a gas (e.g., air), can flow through the distal channel 24, into the cavity 34, and then through the proximal channel 30.

As shown in FIGS. 2-4, the grip element 18 is fixed to the handle body 16 and extends downwardly therefrom. The grip element 18 can comprise any element that facilitates gripping and supporting of the grasper 10 by the user. In the illustrated embodiment, the grip element 18 comprises an elongated member that includes a finger loop 40 similar to that used in scissors through which the user can pass his or her fingers.

Unlike the grip element 18, the actuation lever 20 is pivotable relative to the handle body 16. As shown in FIGS. 2 and 3, the actuation lever 20 includes a circular pivot head 42 that is adapted to be received in the semi-circular cavity 34 formed in the body 16. The head 42 fits within the cavity 34 and is secured to the body 16 with a pivot pin 44 that extends through the body and the head. With such an arrangement, the lever 20 can be pivoted about the pin 44, which acts as the pivot axis of the lever.

Figure 5:
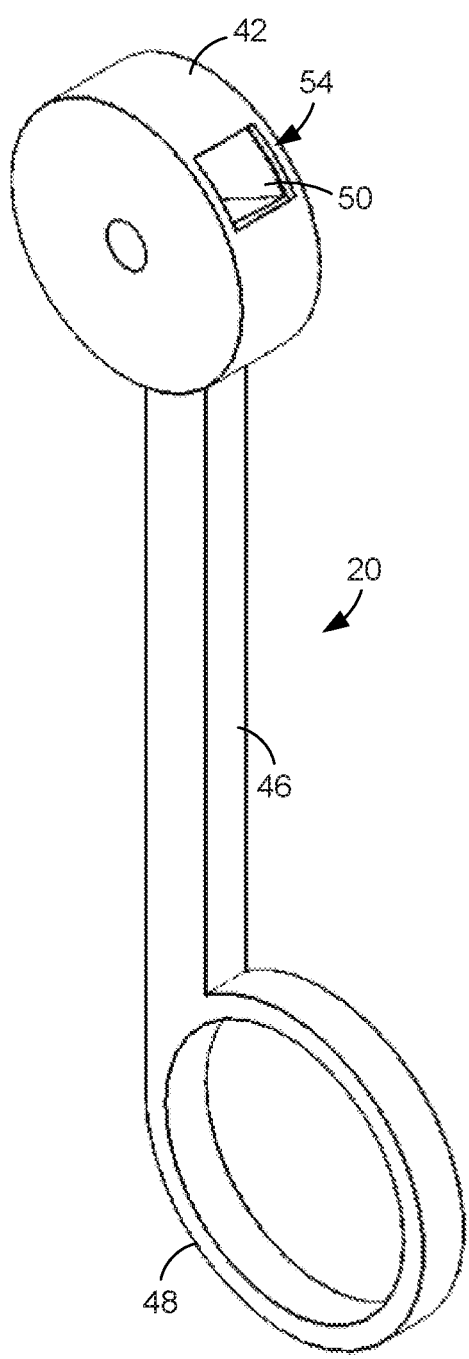
FIG. 5 is a rear perspective view of an actuation lever of the grasper of FIG. 1.
Figure 6:
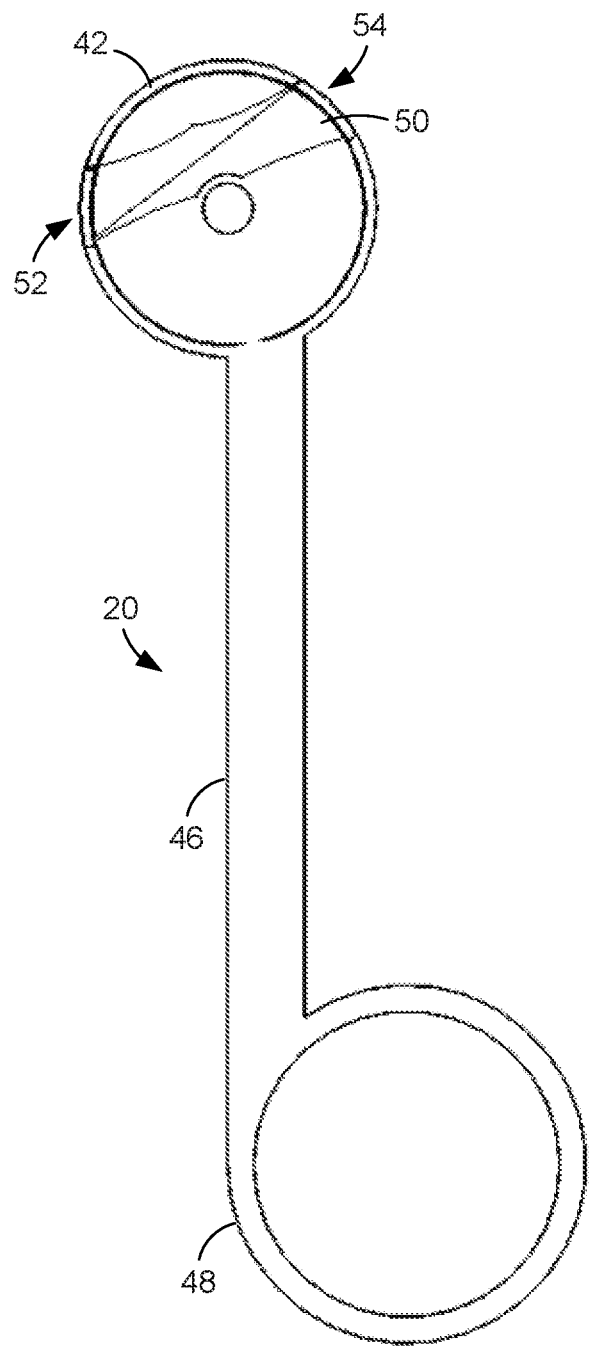
FIG. 6 is a cross-sectional side view of the actuation lever of FIG. 5 taken along a sagittal plane of the grasper.

FIGS. 5 and 6 illustrate the actuation lever 20 separate from the remainder of the grasper 10. As shown in these figures, extending from the pivot head 42 of the lever 20 is an elongated lever arm 46. In the illustrated embodiment, a thumb loop 48 similar to that used in scissors is provided at a distal end of the arm 46 in which the user can place his or her thumb.

Figure 7:
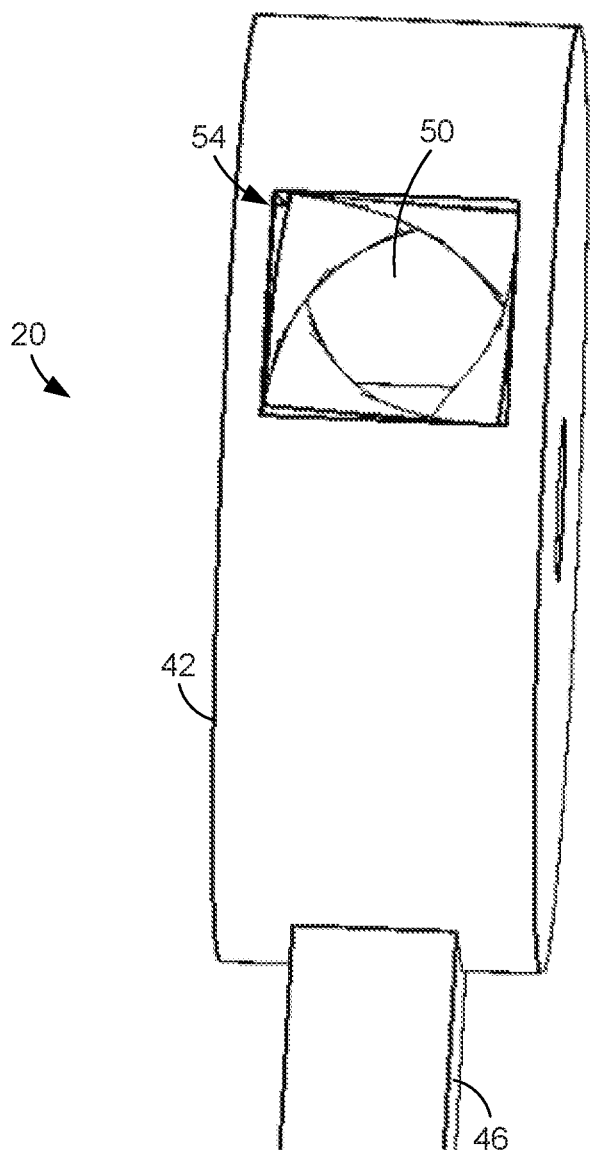
FIG. 7 is a detail view of a pivot head of the actuation lever of FIG. 5, illustrating a central channel of the lever.

As is apparent in FIGS. 5 and 6, a third or central channel 50 is formed through the pivot head 42 of the actuation lever 20. As shown in FIG. 6, this channel 50 can be accessed through an inlet opening 52 provided on the distal side of the head 42 and through an outlet opening 54 provided on the proximal side of the head. In the illustrated embodiment, the inlet and outlet openings 52, 54 are rectangular (e.g., square) as is the channel 50 (in cross-section). With reference to FIG. 7, the channel can, in some embodiments, rotate through 90 degrees from the inlet opening 52 to the outlet opening 54. Although a rectangular channel 50 and openings 52, 54 have been described and illustrated, it is noted that the channel and openings can have other shapes.

As described above, the grasper 10 can be used to grasp patient tissues to manipulate (e.g., refract) them. During such use, a vacuum source can be connected to the outlet port 32 of the handle body 16, so that a fluid, such as air or another gas, can be drawn through the suction head 15, the suction tube 14, and the handle 12. This gas can flow through the internal passage of the handle, which is comprised of the distal channel 24 of the body 16, the central channel 50 of the actuation lever 20, and the proximal channel 30 of the body. However, this flow is only possible when the central channel 50 is aligned with the distal and proximal channels 24 and 30. This alignment is controlled with the actuation lever 20.

In an initial, unactuated position in which no suction force is provided by the grasper 10, the actuation lever 20 is spaced at a maximum distance from the grip element 18. By way of example, the actuation lever 20 can form an approximately 30° angle with the grip element 18 in this position. In some embodiments, the handle 12 includes a biasing element (not shown), such as a compression or tensile spring, that urges the actuation lever 20 into the initial position. An example of such a spring is illustrated below in relation to the second grasper embodiment of FIGS. 9 and 10.

Figure 8:
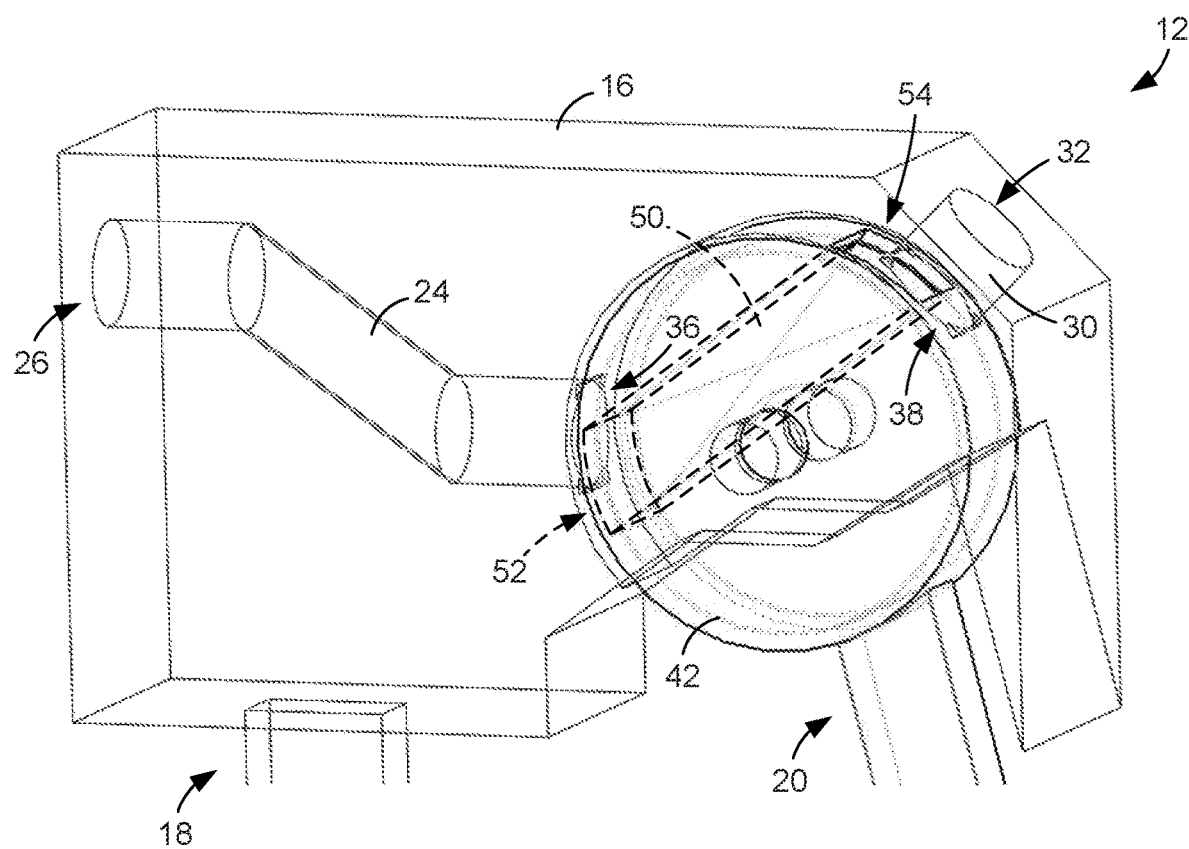
FIG. 8 is a partial perspective wire-frame view of the handle of the grasper of FIG. 1 illustrating internal channels of the grasper aligning to form a continuous internal passage.

While the actuation lever 20 is in the initial position, the central channel 50 of the actuation lever 20 does not align with the proximal channel 30 of the handle body 16. Therefore, no suction force can be provided to the suction head 15. As the actuation lever 20 is pushed forward, however, away from the user and toward the grip element 18, the pivot head 42 of the actuation lever 20 pivots so as to begin to align the central channel 50 with the proximal channel 30 and the distal channel 24. An example of such alignment is shown in FIG. 8. As the channels 24, 50, and 32 align, a continuous internal passage is formed within the handle 12 through which fluid can flow. Accordingly, suction can be provided to the suction head 15.

The amount of suction force that is applied to the suction head 15 and, therefore, the patient tissue, depends upon the degree to which the channels are aligned, which is controlled by the degree to which the actuation lever 20 is pivoted by the user. In FIG. 8, the actuation lever 20 has been pivoted forward several degrees such that the central passage 50 of the pivot head 42 is approximately 50% aligned with the outlet port 36 of the distal channel 24 and the inlet port 38 of the proximal channel 30. Accordingly, an amount of vacuum that is roughly halfway between the minimum and maximum suction that can be applied is being applied. In some embodiments, 100% alignment and maximal vacuum can be achieved when the actuation lever 20 is moved to a position in which it is nearly touching the grip element 18 and/or in which the actuation lever is generally vertical.

It is noted that the simultaneous alignment of the central channel 50 with two other channels 24, 30 makes the increase of suction more linear relative to the angle through which the actuation lever 20 is pivoted. This linearity can be further increased by forming the ports 52, 54 of the central passage 50 to have curved shapes. In some embodiments, the ports 52, 54 can have parabolic shapes (not shown) in which the widths of the ports that are open to the channels 24, 30 continuously increase with increased lever pivoting. When such linearity is achieved, the firmness with which the tissue is grasped can be adjusted by the user using the same type of motions he or she would use to adjust the firmness with which tissue is grasped using a conventional mechanical grasper. This provides greater precision of control to the user and increases the usability of the grasper 10 by making the use of the grasper intuitive and functionally similar to mechanical graspers.

In some embodiments, the grasper 10 can include an internal ratchet mechanism (not shown) that brings operation of the grasper even closer to that of a conventional mechanical grasper. When provided, the ratchet mechanism prevents backward pivoting of the actuation lever 20 from various discrete angular positions to which the lever may be pivoted. With such a feature, the user can set the grasper 10 to a particular level of suction that will be maintained even if the actuation lever 20 is released. If the user wishes to reduce the suction, he or she can do so using a release element associated with the ratchet mechanism.

In further embodiments, the grasper 10 can also include a suction control mechanism (not shown), such as a turnable dial provided on the handle body 16, that sets the maximum suction that can be applied to patient tissue. This limit can be achieved by limiting the vacuum delivered to the grasper 10 or limiting the extent through which the actuation lever 20 can be pivoted. In either case, this mechanism can be used to ensure that a given maximum amount of suction that is to be applied to the tissue is not exceeded. In some embodiments, the mechanism can have various pre-establishing settings for different types of tissues and/or different types of procedures to assist the user in selecting the most appropriate suction level.

In still other embodiments, the grasper 10 or a vacuum system with which it is used can have a mechanism for halting suction for cases in which suction is applied without having an adequate seal with the tissue that is to be manipulated. This feature may be particularly desirable in cases of laparoscopic surgery in which the abdominal cavity is insufflated with a gas, such as carbon dioxide. For example, a pressure sensor can be used to determine how much vacuum is being supplied. If the level is relatively low, it may indicate that a good seal has not been achieved. As a further example, a volume sensor can be used to determine how much gas has been drawn up into the grasper. If the volume is relatively high, it may indicate that a good seal has not been achieved.

In still other embodiments, the grasper 10 can include a mechanism (not shown), such as a dial provided on the body 16, that can be used to rotate the suction tube 14 about its longitudinal axis for the purpose of changing the orientation of the suction head that is mounted to the tube's distal end.

Figure 9:
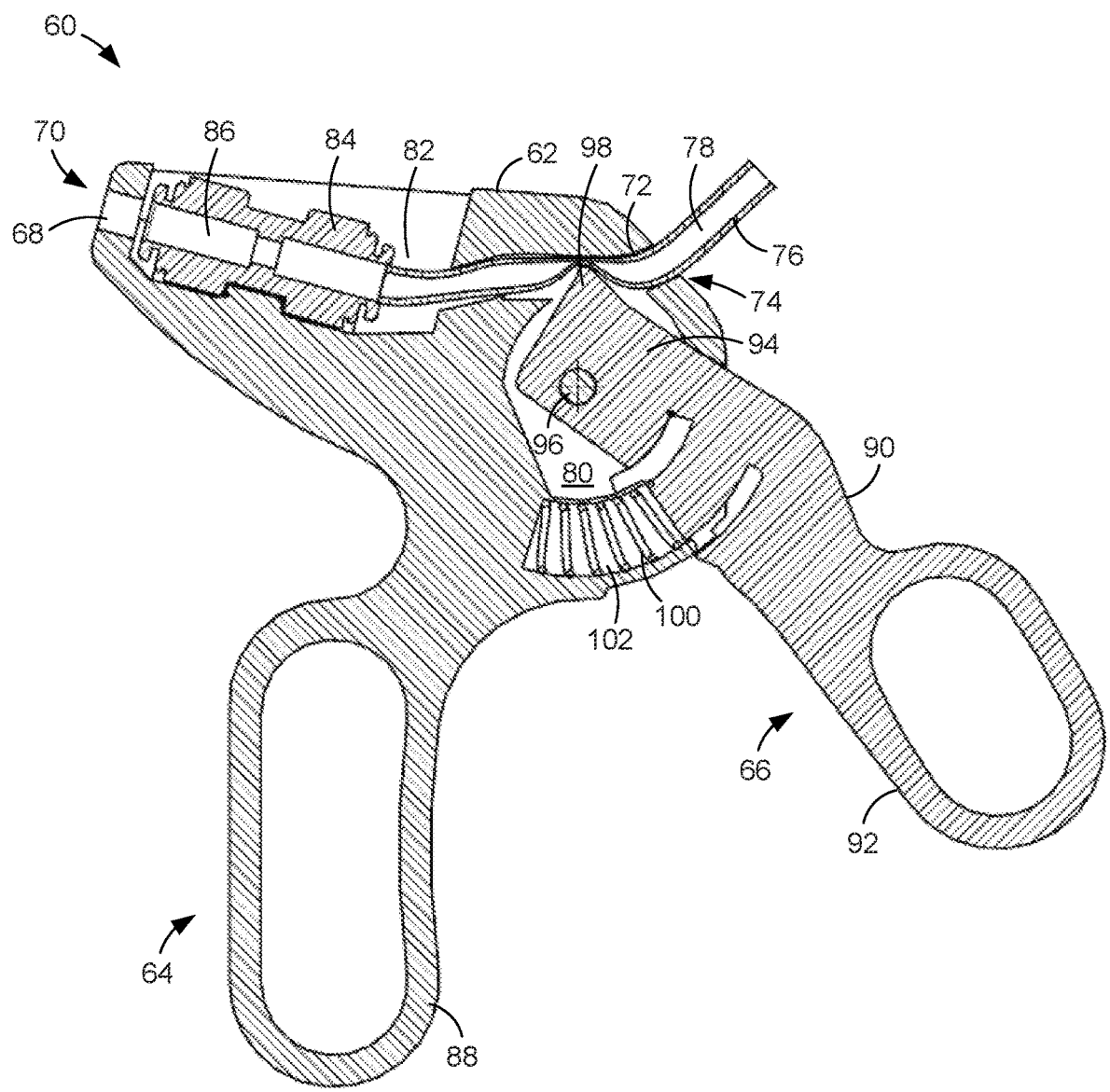
FIG. 9 is a cross-sectional side view of a second embodiment of a vacuum-actuated surgical grasper, the grasper shown in an unactuated position in which no vacuum is applied.
Figure 10:
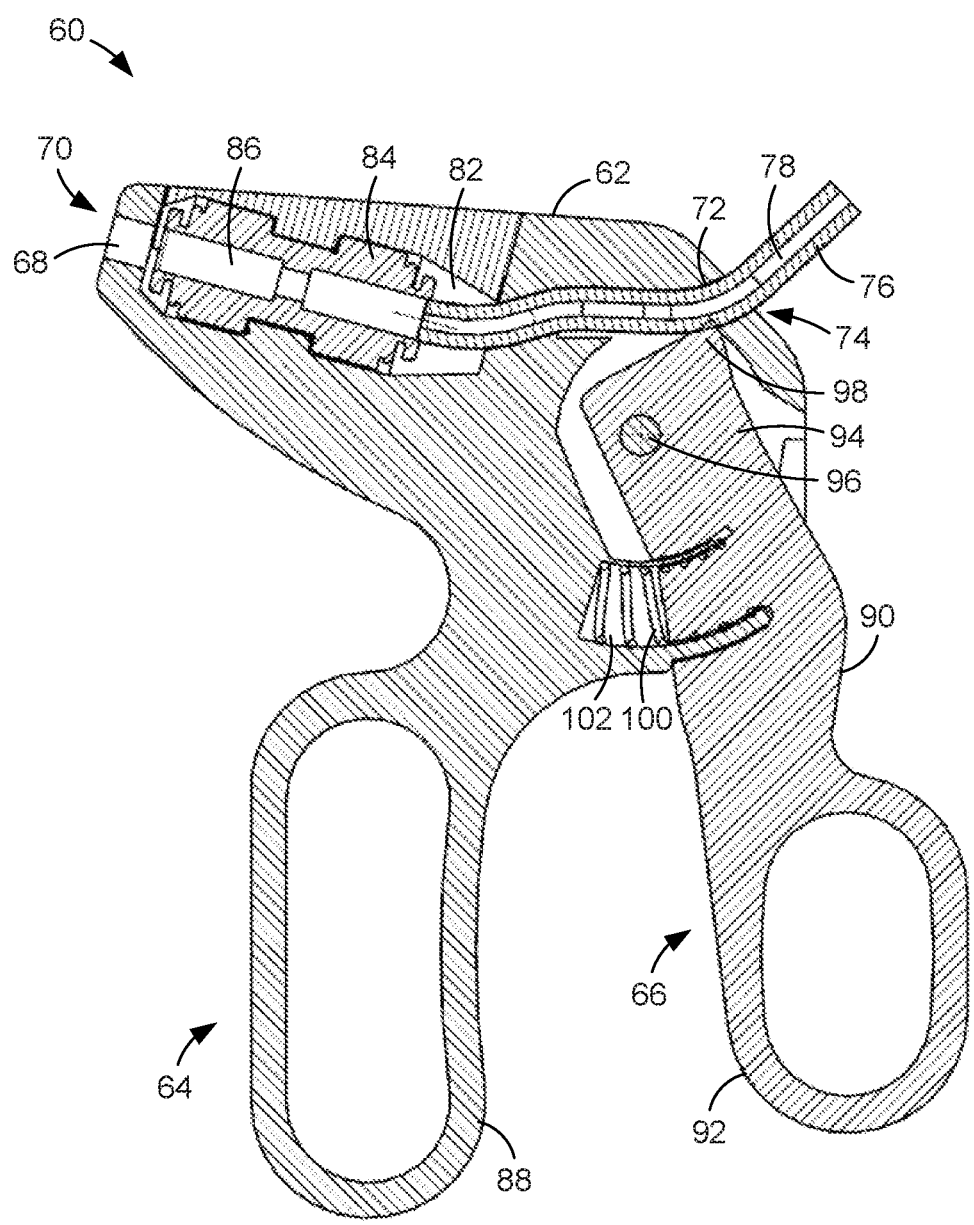
FIG. 10 is a further cross-sectional side view of the grasper of FIG. 9, the grasper shown in activated position in which vacuum is applied.

FIGS. 9 and 10 illustrate a second embodiment of a handle 60 that can be used in a vacuum-actuated surgical grasper. The handle 60 includes many of the features of the handle 12 shown in FIGS. 1-4 and described above. Accordingly, the handle 60 includes a body 62 from which a suction tube (not shown), a grip element 64, and an actuation lever 66 extend. When the vacuum-actuator surgical grasper is fully assembled, the suction tube is placed in fluid communication with an internal passage of the handle 60 that passes through the body 62 through which fluid, such as a gas (e.g., air), can flow to enable the application of suction to a suction head and, therefore, patient tissue.

As indicated in FIGS. 9 and 10, a first or distal channel 68 is formed at the distal end of the body 62 that can be accessed through an inlet port 70 to enable passage of the suction tube. A second or proximal channel 72 is formed at the proximal end of the body 62 that can be accessed through an outlet port 74. Provided in the proximal channel 72 is a flexible vacuum delivery tube 76 that defines an inner flow passage 78 through which the gas can flow. The flexible vacuum delivery tube 76 is made of a resilient material, such as a polymeric material, that can be deformed by a force and return to its original shape after the force is removed. The flexible vacuum delivery tube 76 can either be directly connected to a vacuum source or connected to a further tube that is connected to the vacuum source. As shown in FIG. 9, the flexible vacuum delivery tube 76 extends through the proximal channel 72 and into an upper cavity 80 formed in the body 62. As described below, the flexible vacuum delivery tube 76 is exposed within this cavity 80 to enable opening and closing of the flow passage 78.

The flexible vacuum delivery tube 76 further extends to a distal chamber 82 formed within the body 62. Provided in this chamber 82 is a coupling element 84 that is configured to couple to the flexible vacuum delivery tube 76 at its proximal end and couple to the suction tube (not shown) at its distal end. The coupling element 84 comprises an inner passage 86 through which the gas can flow. Accordingly, gas drawn through the suction tube can enter the distal end of the coupling element 84, travel through the inner passage 86 of the coupling element, and exit the proximal end of the coupling element to deliver the gas to the flow passage 78 of the flexible vacuum delivery tube 76. As such, an internal passage that passes through the handle 60 is formed by the coupling element 84 and the flexible vacuum delivery tube 76.

It is noted that, while a particular coupling element 84 is shown in the drawings and has been described above, in some embodiments, the coupling element can be omitted and either the flexible vacuum delivery tube 76 can directly connect to the suction tube within the body 62 or a different element can be provided in the body to facilitate coupling between the suction tube and the flexible vacuum delivery tube so as to place the suction tube in fluid communication with the source of suction.

As shown in FIGS. 9 and 10, the grip element 64 is fixed to the handle body 62 and extends downwardly therefrom. The grip element 18 can comprise any element that facilitates gripping and supporting of the grasper by the user. In the illustrated embodiment, the grip element 64 comprises an elongated member that includes a finger loop 88 similar to that used in scissors through which the user can pass his or her fingers.

The actuation lever 66 comprises an elongated lever arm 90. In the illustrated embodiment, a thumb loop 92 similar to that used in scissors is provided at a distal end of the arm 90 in which the user can place his or her thumb. Unlike the grip element 64, the actuation lever 66 is pivotable relative to the handle body 62. As shown in the figures, the actuation lever 66 includes a pivot head 94 that is adapted to be received in the upper cavity 80 formed in the body 62. The head 94 fits within the cavity 80 and is secured to the body 62 with a pivot pin 96 that extends through the body and the head. With such an arrangement, the lever 66 can be pivoted about the pin 96, which acts as the pivot axis of the lever.

Formed at the tip of the pivot head 94 is a tube engagement element 98 that is configured to engage the flexible vacuum delivery tube 76. More particularly, the tube engagement element 98 is configured to selectively pinch or crimp the flexible vacuum delivery tube 76 so as to partially or totally close the tube's flow passage 78 to thereby partially or completely block flow through the passage, depending upon the actuation state of the handle 66. In some embodiments, the tube engagement element 98 is formed as a cam having a cam surface that has a maximum radius at its proximal end that gradually decreases to a minimum radius at its distal end.

With further reference to the figures, the handle 60 also includes a biasing element 100, in the form of a coil spring, which urges the actuation lever 66 away from the grip element 64. This biasing element 100 is contained in a lower cavity 102. The cavity's distal end abuts the body 62 while its proximal end abuts the actuation lever 66. With this positioning, the biasing element 100 acts to provide resistance to pivoting of the actuation lever 66 toward the grip element 64 by a user and returns the actuation lever to its initial position when a pivoting force is no longer applied by the user.

FIGS. 9 and 10, when considered together, illustrate operation of the handle 60. FIG. 9 shows the handle 60 in an initial, unactuated position. In this position, the actuation lever 66 is positioned at a maximum distance away from the grip element 64 under the force of the biasing element 100. While the actuation lever 66 is in this position, the tube engagement element 98 of the lever is pressed into firm contact with the flexible vacuum delivery tube 76, thereby causing the tube to deform (collapse) and close the tube's flow passage 78. When the flow passage 78 is closed as shown in FIG. 9, no gas can flow through the flexible vacuum delivery tube 76 and no suction can be applied by the suction head to patient tissue. As the actuation lever 66 is pushed forward, however, away from the user and toward the grip element 64, the tube engagement element 98 of the actuation lever 66 is pivoted away from the flexible vacuum delivery tube 76 so as to gradually enable the flow passage 78 to open and create a continuous internal within the handle 12 through which fluid can flow. Accordingly, suction can be provided to the suction head.

The amount of suction force that is applied to the suction head and, therefore, the patient tissue, depends upon the degree to which the actuation lever 66 is pivoted by the user. In FIG. 10, the actuation lever 66 has been pivoted to its forward-most position in which the tube engagement element 98 either does not or only slightly deforms the flexible vacuum delivery tube. In this position, the flow passage 78 of the flexible vacuum delivery tube is either completely or nearly completely open, thereby enabling the maximum amount of vacuum to the suction head.

When the tube engagement element 98 is formed as a cam having a decreasing radius (at the contact point with the flexible vacuum delivery tube 76 as the actuation lever 66 is moved forward), the suction strength can linearly increase. When such linearity is achieved, the firmness with which the tissue is grasped can be adjusted by the user in similar manner to the firmness with which tissue can be grasped using a conventional mechanical grasper.

As with the handle 12, the handle 60 can include other features. Such features can include an internal ratchet mechanism that prevents backward pivoting of the actuation lever 66 from various discrete angular positions to which the lever may be pivoted, a suction control mechanism that sets the maximum suction that can be applied to patient tissue, a mechanism that halts suction for cases in which suction is applied without having an adequate seal with the tissue that is to be manipulated, and a mechanism that can be used to rotate the suction tube about its longitudinal axis for the purpose of changing the orientation of the suction head that is mounted to the tube's distal end.

Figure 11:
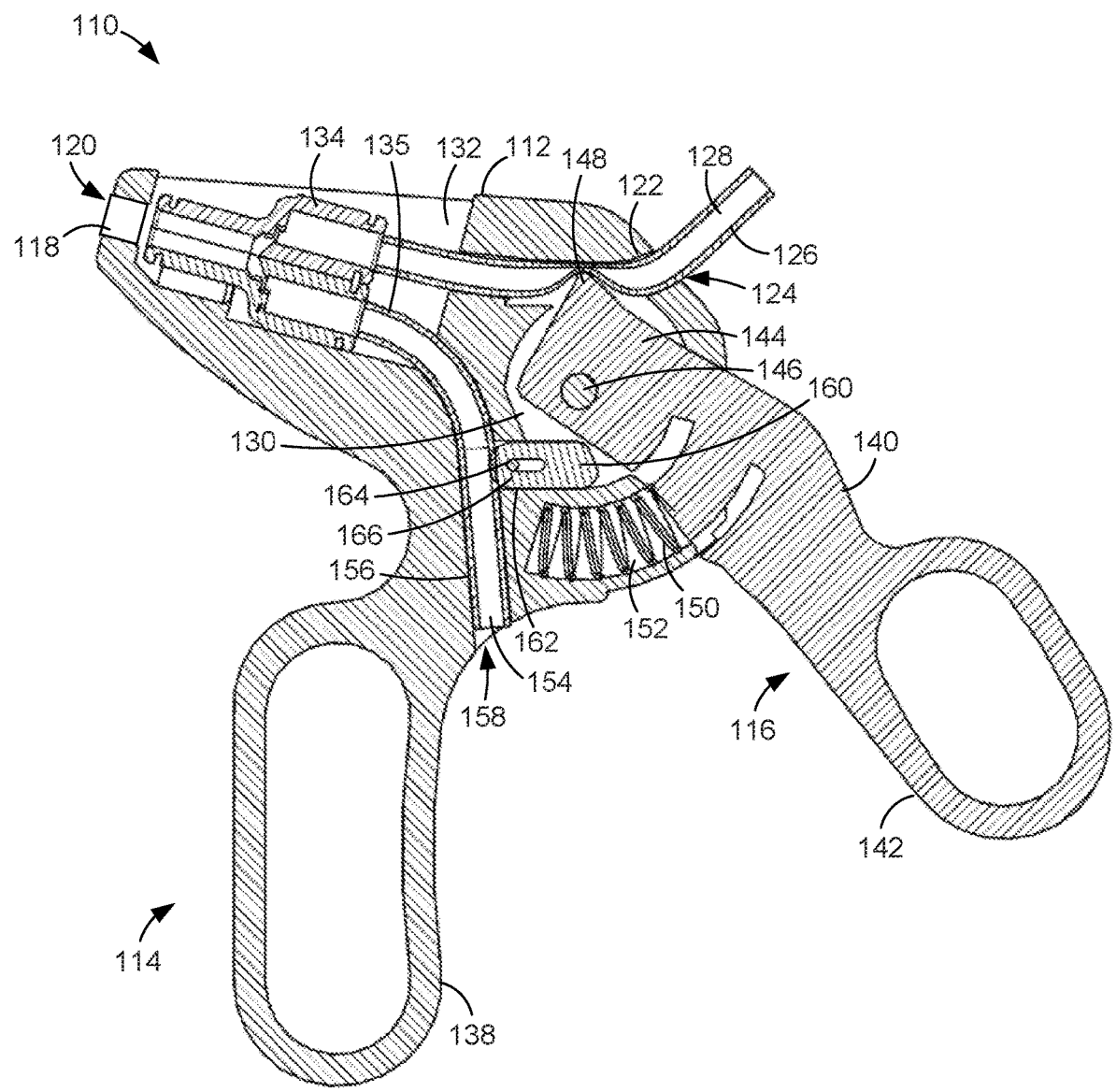
FIG. 11 is a cross-sectional side view of a third embodiment of a vacuum-actuated surgical grasper, the grasper shown in an unactuated position in which no vacuum is applied.
Figure 12:
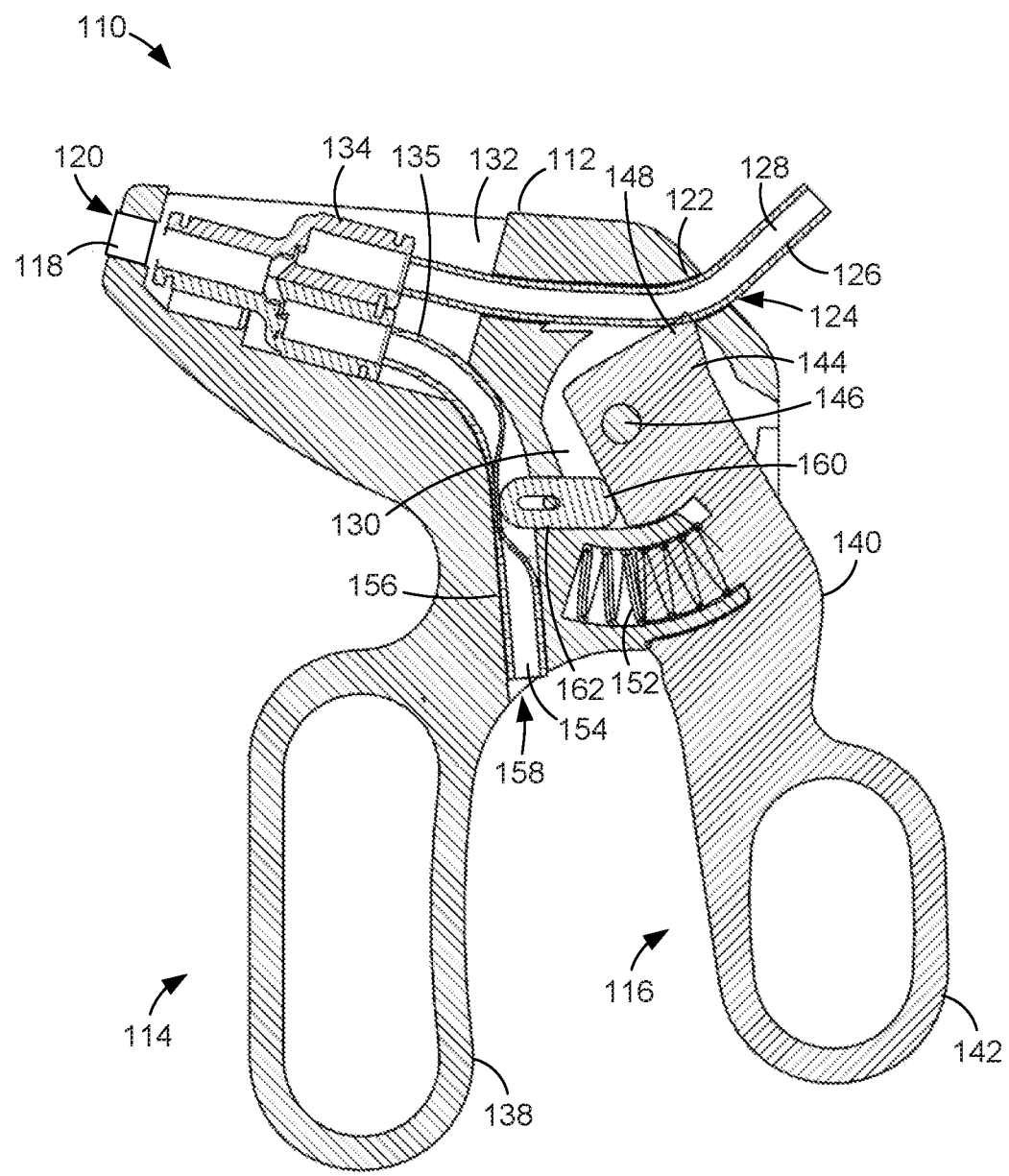
FIG. 12 is a further cross-sectional side view of the grasper of FIG. 11, the grasper shown in activated position in which vacuum is applied.

FIGS. 11 and 12 illustrate a third embodiment of a handle 110 that can be used in a vacuum-actuated surgical grasper. The handle 110 is similar to the handle 60 shown in FIGS. 9 and 10. Accordingly, the handle 110 includes a body 112 from which a suction tube (not shown), a grip element 114, and an actuation lever 116 extend. When the vacuum-actuated surgical grasper is fully assembled, the suction tube is placed in fluid communication with an internal passage of the handle 110 that passes through the body 112 through which fluid, such as a gas (e.g., air), can flow to enable the application of suction to a suction head and, therefore, patient tissue.

As indicated in FIGS. 11 and 12, a first or distal channel 118 is formed at the distal end of the body 112 that can be accessed through an inlet port 120 to enable passage of the suction tube. A second or proximal channel 122 is formed at the proximal end of the body 112 that can be accessed through an outlet port 124. Provided in the proximal channel 122 is a flexible vacuum delivery tube 126 that defines an inner flow passage 128 through which the gas can flow. As shown in the figures, the flexible vacuum delivery tube 126 extends through the proximal channel 122, through an upper cavity 130 formed in the body 112, and to a distal chamber 132 formed within the body. Provided in this chamber 132 is a coupling element 134. In the embodiment of FIGS. 11 and 12, the coupling element 134 is configured as a T-shaped coupler that connects to the suction tube at its distal end and connects to the flexible vacuum delivery tube 126 at its proximal end. The coupling element 134 further connects to a flexible vent tube 135, which is described below. The coupling element 134 forms two inner passages, one that extends from the distal end (and the suction tube) to the flexible vacuum delivery tube 126 and one that extends from the distal end (and the suction tube) to the flexible vent tube 135. Accordingly, gas can flow into the flexible vacuum delivery tube 126 from either or both of the suction tube and the flexible vent tube 135.

As shown in FIGS. 11 and 12, the grip element 114 is fixed to the handle body 112 and extends downwardly therefrom. The grip element 114 can comprise any element that facilitates gripping and supporting of the grasper by the user. In the illustrated embodiment, the grip element 114 comprises an elongated member that includes a finger loop 138 similar to that used in scissors through which the user can pass his or her fingers.

The actuation lever 116 comprises an elongated lever arm 140. In the illustrated embodiment, a thumb loop 142 similar to that used in scissors is provided at a distal end of the arm 140 in which the user can place his or her thumb. The actuation lever 116 is pivotable relative to the handle body 112 and includes a pivot head 144 that is adapted to be received in the upper cavity 130 formed in the body 112. The head 144 fits within the cavity 130 and is secured to the body 112 with a pivot pin 146 that extends through the body and the head. With such an arrangement, the lever 116 can be pivoted about the pin 146, which acts as the pivot axis of the lever.

Formed at the tip of the pivot head 144 is a tube engagement element 148 that is configured to engage the flexible vacuum delivery tube 126. More particularly, the tube engagement element 148 is configured to pinch or crimp the flexible vacuum delivery tube 126 so as to partially or totally close the tube's flow passage 128 to thereby partially or completely block flow through the passage, depending upon the actuation state of the handle 110. In some embodiments, the tube engagement element 148 comprises a cam having a cam surface that has a maximum radius at its proximal end that gradually decreases to a minimum radius at its distal end.

With further reference to the figures, the handle 110 also includes a biasing element 150, in the form of a coil spring, which urges the actuation lever 116 away from the grip element 114. This biasing element 150 is contained in a lower cavity 152. The cavity's distal end abuts the body 112 while its proximal end abuts the actuation lever 116. With this positioning, the biasing element 150 acts to provide resistance to pivoting of the actuation lever 116 toward the grip element 114 by a user and returns the actuation lever to its initial position when a pivoting force is no longer applied by the user.

With reference to FIG. 11, the flexible vent tube 135 includes a gas flow passage 154 through which gas can flow. The flexible vent tube 135 extends from the distal chamber 132 through a further channel 156 that extends downwardly through the body 112 of the handle 110 and opens to the atmosphere via a further port 158. As such, the coupling element 134 is placed in fluid communication with the atmosphere, as least in the initial, unactuated position of the actuation lever 116 illustrated in FIG. 11, via the flow passage 154 of the flexible vent tube 135.

As is also shown in FIG. 11, the handle 110 further includes a tube engagement member 160 that is positioned within a medial channel 162 that extends forward from the cavity 130. The tube engagement member 160 is retained in the medial channel 162 by a pin 164 that is positioned within an elongated slot 166 formed in the tube engagement member. The tube engagement member 160 can freely slide along the medial channel 162 and can be urged into varying degrees of contact with the flexible vent tube 135 by pivoting of the actuation lever 116.

FIGS. 11 and 12, when considered together, illustrate operation of the handle 110. FIG. 11 shows the handle 110 in an initial, unactuated position. In this position, the actuation lever 116 is positioned at a maximum distance away from the grip element 114 under the force of the biasing element 150. While the actuation lever 116 is in this position, the tube engagement element 148 of the lever is pressed into firm contact with the flexible vacuum delivery tube 126, thereby causing the tube to deform (collapse) and close the tube's flow passage 128. Because the flow passage 128 is closed, no gas can flow through the flexible vacuum delivery tube 126 and no suction can be applied by the suction head to patient tissue. In contrast, the flexible vent tube 135 and its flow passage 154 are left open as the tube engagement member 160 is not pressed into firm contract with the flexible vent tube in the orientation of FIG. 11. As such, the suction tube (not shown) is open to the atmosphere.

As the actuation lever 116 is pushed forward, away from the user and toward the grip element 114, the tube engagement element 148 of the actuation lever 116 is pivoted away from the flexible vacuum delivery tube 126 so as to gradually enable the flow passage 128 to open and create a continuous internal within the handle 110 through which fluid can flow. Simultaneously, the tube engagement member 160 is pressed into firm contact with the flexible vent tube 135, thereby causing the tube to deform (collapse) and close the tube's flow passage 154. In other words, as the actuation lever 116 is pushed forward, the flow passage 128 of the flexible vacuum delivery tube 126 is gradually opened while the flow passage 154 of the flexible vent tube 135 is gradually closed. The vacuum pressure provided to the suction head is attenuated to a degree by the fluid flow through the flexible vent tube 135. This fluid flow can range from a minimum vacuum pressure applied at the suction head when the flow passage 154 is in the fully open configuration to a maximum vacuum pressure when the flow passage 154 is fully closed. Moving the actuation lever 116 forward simultaneously increases access to vacuum pressure by opening the flow passage 128 and decreases the attenuation of vacuum pressure by closing the flow passage 154, enabling the maximum vacuum pressure to be reached in a significantly more controlled, gradual, and linear manner.

As with the other disclosed handles 12, 60, the handle 110 can include other features. Such features can include an internal ratchet mechanism that prevents backward pivoting of the actuation lever 116 from various discrete angular positions to which the lever may be pivoted, a suction control mechanism that sets the maximum suction that can be applied to patient tissue, a mechanism that halts suction for cases in which suction is applied without having an adequate seal with the tissue that is to be manipulated, and a mechanism that can be used to rotate the suction tube about its longitudinal axis for the purpose of changing the orientation of the suction head that is mounted to the tube's distal end.

The invention claimed is:

1. A vacuum-assisted surgical grasper comprising:
a suction head adapted to grasp patient tissue using only suction;
a suction tube connected to and in fluid communication with the suction head; and
a handle connected to the suction tube, the handle comprising a body including an internal cavity, a fixed grip element extending downward from the body and configured to be gripped by fingers of the user, and a pivotable actuation lever extending downward from the body and configured to be actuated by the user's thumb, the actuation lever including a pivot head about which the actuation lever can be pivoted, the body including an internal passage having a flexible vacuum delivery tube that extends through the internal cavity and is in fluid communication with the suction tube through which fluid from the suction tube can flow and a coupling element that connects the vacuum delivery tube to the suction tube, wherein flow through the internal passage and grasping of the patient tissue are enabled by the user by pivoting the actuation lever toward the grip element using the thumb,
wherein the actuation lever further includes a tube engagement element that is provided within the internal cavity and configured to crimp the vacuum delivery tube when the actuation lever is in an initial, unactuated position so as to preclude fluid flow through the vacuum delivery tube and wherein pivoting of the actuation lever about the pivot head moves the tube engagement element away from the vacuum delivery tube so as to enable fluid flow through the vacuum delivery tube, and
wherein the handle further comprises a flexible vent tube also in fluid communication with the suction tube.

2. The grasper of claim 1, further comprising a tube engagement member provided within the handle body, wherein the tube engagement member is urged into the flexible vent tube by the actuation lever when the actuation lever is pivoted away from the initial, unactuated position such that the tube engagement member crimps the flexible vent tube as the lever is pivoted to limit fluid flow through the flexible vent tube.

3. The grasper of claim 2, wherein a suction force applied by the suction head increases linearly as the actuation lever is pivoted away from the initial, unactuated position.

4. The grasper of claim 2, wherein the handle further comprises a biasing element that biases the actuation lever toward the initial, unactuated position.

\* \* \* \* \*